United States Patent
Assmann et al.

(10) Patent No.: US 6,214,840 B1
(45) Date of Patent: Apr. 10, 2001

(54) ANNULATED AZOLE DERIVATIVES USEFUL AS MICROBICIDAL AGENTS

(75) Inventors: Lutz Assmann, St. Peter-Ording; Hans-Ludwig Elbe, Wuppertal; Ralf Tiemann, Leverkusen; Klaus Stenzel, Düsseldorf, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/380,502

(22) PCT Filed: Feb. 19, 1998

(86) PCT No.: PCT/EP98/00942

§ 371 Date: Sep. 3, 1999

§ 102(e) Date: Sep. 3, 1999

(87) PCT Pub. No.: WO98/39331

PCT Pub. Date: Sep. 11, 1998

(30) Foreign Application Priority Data

Mar. 4, 1997 (DE) .............................. 197 08 688

(51) Int. Cl.⁷ .................... A01N 43/90; C07D 471/04
(52) U.S. Cl. ........................... 514/303; 546/118
(58) Field of Search .............................. 546/118; 514/303

(56) References Cited

U.S. PATENT DOCUMENTS

| | | | |
|---|---|---|---|
| 4,579,853 | 4/1986 | Giraudon et al. | 514/303 |
| 4,734,427 | 3/1988 | Riebel et al. | 514/398 |
| 5,322,853 | 6/1994 | Ackermann et al. | 514/359 |
| 5,369,086 | 11/1994 | James et al. | 504/253 |
| 5,504,214 | 4/1996 | Marhold et al. | 548/259 |

FOREIGN PATENT DOCUMENTS

| | | |
|---|---|---|
| 19523446 | 1/1997 | (DE) . |
| WO 96/32395 | * 10/1996 | (WO) . |
| 97/01561 | 1/1997 | (WO) . |
| WO 97/06171 | * 2/1997 | (WO) . |

OTHER PUBLICATIONS

J. Heterocyclic Chem., 18, 997, Aug. 1981. pp. 997–1006, Some Heterocyclic Sulfonyl Chlorides and Derivatives, Richard J. Cremlyn, Fred. J. Swinbourne and Kin–Man Yung.
Chemische Berichte, 85, Apr. 1952, pp. 1012–1020, Freidhelm Korte: Synthese purinähnlicher Heterocyclen.
Arch. Pharm. 290 (month unavailable) 1957, pp. 20–31, Synthese von 2–Oxy–imidazolo–(5', 4':2–3)–pyridinen), Alfred Dornow und Otto Hahmann
Chem. Ber. 60, (month unavailable) 1927, pp. 771–775.
V.N. Bobkov et al, Chem. Heterocycl. Comp. (month unavailable) 1991, pp. 1285–1288 XP–002068201, Reaction of 8–Bromothophylline with Pyridine and Alkylpyridines. 8–Pyridiniotheophtllinates

* cited by examiner

Primary Examiner—Patricia L. Morris
(74) Attorney, Agent, or Firm—Joseph C. Gil

(57) ABSTRACT

Novel fused azole derivatives of the formula (I)

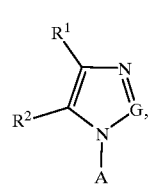

in which
$R^1$, $R^2$, A and G are as defined in the description,
and also their acid addition salts and metal salt complexes, a plurality of processes for preparing these substances and their use as microbicides in crop protection and in the protection of materials.

5 Claims, No Drawings

ANNULATED AZOLE DERIVATIVES USEFUL AS MICROBICIDAL AGENTS

The present invention relates to novel fused azole derivatives, to a plurality of processes for their preparation and to their use as microbicides in crop protection and in the protection of materials.

It is already known that certain fused azole derivatives have fungicidal properties (cf. DE-A 195 23 446). Thus, for example, 1-(3,5-dimethyl-isoxazol-4-sulphonyl)-1H-benzotriazole can be employed for controlling fungi. The activity of this substance is good but in some cases unsatisfactory at low application rates.

This invention, accordingly, provides novel fused azole derivatives of the formula

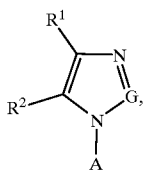

(I)

in which
$R^1$ and $R^2$ together with the carbon atoms to which they are attached represent an optionally substituted heterocyclic ring or represent an optionally substituted benzo-fused heterocyclic ring,
G represents nitrogen or a grouping

in which
R3 represents hydrogen, halogen, cyano, nitro, trifluoromethyl, thiocarbamoyl, thiocyanato or the grouping

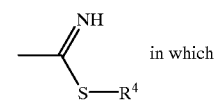

$R^4$ represents alkyl,
A represents one of the following groupings

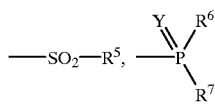

in which
Y represents oxygen or sulphur,
R5 represents an optionally substituted, unsaturated heterocyclic radical,
R6 and R7 independently of one another represent alkyl, halogenoalkyl, alkoxy, halogenoalkoxy, alkylthio, halogenoalkylthio, alkenyl, halogenoalkenyl, alkenyloxy, alkenylthio, alkinyl, alkinyloxy, alkinylthio, optionally alkyl-, cycloalkyl- or aryl-substituted amino, optionally substituted aryl, optionally substituted aryloxy, optionally substituted arylthio, optionally substituted cycloalkyl, optionally substituted cycloalkyloxy, optionally substituted cycloalkylthio or represents an optionally substituted, saturated or unsaturated heterocyclic radical, or
R6 and R7 together with the phosphorus atom to which they are attached represent an optionally substituted heterocyclic radical,
and also their acid addition salts and metal salt complexes.

In the definitions, the saturated or unsaturated hydrocarbon chains, such as alkyl, alkenyl or alkinyl, are in each case straight-chain or branched, including in combination with heteroatoms, such as in alkoxy, alkylthio or alkylamino.

Furthermore, it has been found that the fused azole derivatives of the formula (I) and also their acid addition salts and metal salt complexes are obtained when a) azoles of the formula

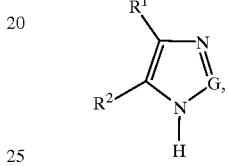

(II)

in which
$R^1$, $R^2$ and G are as defined above
are reacted with halides of the formula

A—X¹ (III)

in which
A is as defined above and
X¹ represents halogen,
if appropriate in the presence of an acid binder and if appropriate in the presence of a diluent,
or when b) cyanoimidazoles of the formula

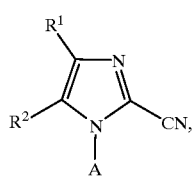

(I-a)

in which
$R^1$, $R^2$ and A are as defined above
reacted with hydrogen sulphide, if appropriate in the presence of a base and if appropriate in the presence of a diluent,
or when c) thiocarbamoylimidazoles of the formula

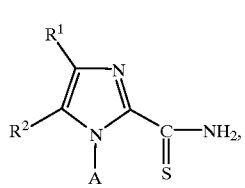

(I-b)

in which $R^1$, $R^2$ and A are as defined above
are reacted with an alkylating agent of the formula $$R^4\text{—}X^2 \qquad (IV)$$

in which
  $R^4$ is as defined above and
  $X^2$ represents a leaving group,
if appropriate in the presence of an acid binder and if appropriate in the presence of a diluent,
and an acid or a metal salt is added, if appropriate, to the resulting compounds of the formula (I).

Finally, it has been found that the fused azole derivatives of the formula (1) and also their acid addition salts and metal salt complexes have very good microbicidal properties and can be employed both in crop protection and in the protection of materials.

Surprisingly, the substances according to the invention have better fungicidal activity than 1-(3,5-dimethyl-isoxazole-4-sulphonyl)-1H-benzotriazole, which is an active compound of the prior art having similar constitution and the same direction of action.

The formula (I) provides a general definition of the substances according to the invention.

$R^1$ and $R^2$ together with the carbon atoms to which they are attached preferably represent a 5- or 6-membered heterocyclic ring which contains one, two or three identical or different heteroatoms, such as oxygen, sulphur and/or nitrogen, and may be mono- to trisubstituted by identical or different substituents selected from the group consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms, in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and halogenoalkylcarbonyloxy having 1 to 4 carbon atoms in the halogenoalkyl group and 1 to 5 identical or different halogen atoms, or $R^1$ and $R^2$ together with the carbon atoms to which they are attached preferably represent a benzo-fused 5- or 6-membered heterocyclylic ring which contains one or two identical or different heteroatoms, such as oxygen, sulphur and/or nitrogen, and may be mono- to trisubstituted by identical or different substituents selected from the group consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and halogenoalkylcarbonyloxy having 1 to 4 carbon atoms in the halogenoalkyl group and 1 to 5 identical or different halogen atoms,
  where, if the heterocyclic ring or the benzo-fused heterocyclic ring contains more than one oxygen atom, the oxygen atoms are not adjacent G also preferably represents nitrogen or a grouping

$R^3$ preferably represents hydrogen, fluorine, chlorine, bromine, iodine, cyano, nitro, trifluoromethyl, thiocarbamoyl, thiocyanato or the grouping

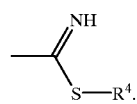

$R^4$ preferably represents alkyl having 1 to 4 carbon atoms.
A also preferably represents one of the following groupings:

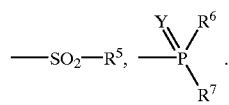

Y also preferably represents oxygen or sulphur.
$R^5$ preferably represents an unsaturated heterocyclyl radical having 5 or 6 ring members and 1 to 3 identical or different heteroatoms, such as nitrogen, oxygen and/or sulphur, where each of the heterocyclyl radicals may be mono- or disubstituted by identical or different substituents selected from the group consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkylcarbonyloxy having 1 to 4 carbon atoms in the alkyl moiety and halogenoalkylcarbonyloxy having 1 to 4 carbon atoms in the halogenoalkyl group and 1 to 5 identical or different halogen atoms.

$R^6$ and $R^7$ independently of one another preferably represent straight-chain or branched alkyl having 1 to 4 carbon atoms, straight-chain or branched halogenoalkyl having 1 to 4 carbon atoms and 1 to 5 identical or different halogen atoms, straight-chain or branched alkoxy having 1 to 4 carbon atoms, straight-chain or branched halogenoalkoxy having 1 to 4 carbon atoms and 1 to 5 identical or different halogen atoms, straight-chain or branched alkylthio having 1 to 4 carbon atoms, straight-chain or branched halogenoalkylthio having 1 to 4 carbon atoms and 1 to 5 identical or different halogen atoms, straight-chain or branched alkenyl having 2 to 4 carbon atoms, straight-chain or branched halogenoalkenyl having 2 to 4 carbon atoms and 1 to 5 identical or different halogen atoms, straight-chain or branched alkenyloxy having 2 to 4 carbon atoms, straight-chain or branched alkenylthio having 2 to 4 carbon atoms, straight-chain or branched alkinyl having 2 to 4 carbon atoms, straight-chain or branched alkinyloxy having 2 to 4 carbon atoms, straight-chain or branched alkinylthio having 2 to 4 carbon atoms, amino which is optionally mono- or disubstituted by identical or different substituents selected from the group consisting of alkyl having 1 to 4 carbon atoms, cycloalkyl having 3 to 7 carbon atoms and phenyl, or represent phenyl, phenoxy, phenylamino or phenylthio, where each of these radicals may be mono- to trisubstituted by identical or different substituents selected from the group consisting of fluorine, chlorine, bromine, alkyl having 1 to 4 carbon atoms, halogenoalkyl having 1 to 4 carbon atoms and 1 to 5 fluorine, chlorine and/or bromine atoms, alkoxy having 1 to 4 carbon atoms and halogenoalkoxy having 1 to 4 carbon atoms and 1 to 5 fluorine, chlorine and/or bromine atoms, or represent cycloalkyl having 3 to 7 carbon atoms, cycloalkyloxy having 3 to 7 carbon atoms, cycloalkylthio having 3 to 7 carbon atoms, cycloalkylamino having 3 to 7 carbon atoms, pyrrolidinyl, piperidinyl or morpholinyl, where each of the abovementioned radicals may be mono- to trisubstituted by identical or different substituents selected from the group consisting of fluorine, chlorine, bromine, alkyl having 1 to 4 carbon atoms and halogenoalkyl having 1 to 4 carbon atoms and 1 to 5 fluorine, chlorine and/or -bromine atoms, or represent a saturated or unsaturated heterocyclyl radical having 5 or 6 ring members and 1 to 3 identical or different heteroatoms, such as nitrogen, oxygen and/or sulphur, where each of these radicals may be mono- or disubstituted by identical or different substituents selected from the group consisting of halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, hydroximinoalkyl having 1 to 4 carbon atoms in the alkyl moiety, alkoximinoalkyl having 1 to 4 carbon atoms in the alkoxy moiety and 1 to 4 carbon atoms in the alkyl moiety, alkyl carbonyloxy having 1 to 4 carbon atoms in the alkyl moiety and halogenoalkylcarbonyloxy having 1 to 4 carbon atoms in the halogenoalkyl group and 1 to 5 identical or different halogen atoms.

$R^6$ and $R^7$ furthermore together with the phosphorus atom to which they are attached preferably represent a 5- or 6-membered heterocyclyl radical which may contain one or two other identical or different heteroatoms, such as oxygen, sulphur and/or nitrogen, and may be mono- to trisubstituted by identical or different substituents selected from the group consisting of fluorine, chlorine, bromine, alkyl having 1 to 4 carbon atoms, alkoxy having 1 to 4 carbon atoms and halogenoalkoxy having 1 to 4 carbon atoms and 1 to 5 fluorine, chlorine and/or bromine atoms.

$R^1$ and $R^2$ together with the carbon atoms to which they are attached represent in particular furandiyl, thiophenediyl, pyrrolediyl, oxazolediyl, thiazolediyl, imidazolediyl, isoxazolediyl, isothiazolediyl, pyrazolediyl, 1,2,3oxadiazolediyl, 1,2,3-thiadiazolediyl, 1,2,3-triazolediyl, pyridinediyl, pyridazinediyl, pyrazinediyl, pyrimidinediyl, 1,2,4-triazinediyl, indole-2,3diyl, benzofuran-2,3-diyl, benzothiophene-2,3-diyl, quinoline-2,3-diyl, quinazoline-2,3-diyl, benzo[1,4]dioxine-2,3-diyl, benzo[1,4]dithiine-2,3-diyl, 4H-benzo[1,4]oxazine-2,3-diyl, 4H-benzo[1,4]thiazine-2,3-diyl, where these radicals may be mono- or disubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and ethoxyiminoethyl, or $R^1$ and $R^2$ together represent a radical of the formula

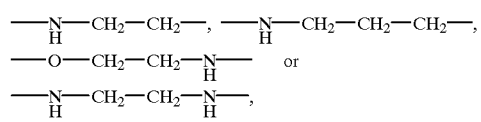

where each of these radicals may be mono- or disubstituted by methyl.

G also in particular represents nitrogen or a grouping

$R^3$ also in particular represents hydrogen, fluorine, chlorine, bromine, iodine, cyano, nitro, trifluoromethyl, thiocarbamoyl, thiocyanato or the grouping

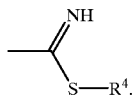

$R^4$ represents in particular methyl or ethyl.
A also in particular represents one of the following groupings:

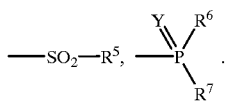

Y also in particular represents oxygen or sulphur.
$R^5$ represents in particular pyrrolyl, furyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridyl, pyrimidyl, pyrazinyl or pyridazinyl,
where each of these radicals may be mono- or disubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio,, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, -methoxyiminoethyl and ethoxyiminoethyl.
$R^6$ and $R^7$ independently of one another represent in particular methyl, ethyl, n- or i-propyl, n-, i-, s- or t-butyl, trifluoromethyl, trifluoroethyl, methoxy, ethoxy, nor i-propoxy, n-, i-, s- or t-butoxy, difluoromethoxy, trifluoromethoxy, difluorochloromethoxy, trifluoroethoxy, methylthio, ethylthio, n- or 1propylthio, difluoromethylthio, trifluoromethylthio, difluorochloromethylthio, allyl, n- or s-butenyl; allyloxy, n- or s-butenyloxy; allylthio, n- or s-butenylthio; propargyl, n- or s-butinyl; propargyloxy; propargylthio; amino; methylamino, ethylamino, n- or i-propylamino, n-, i-, s- or t-butylamino; dimethylamino, diethylamino, di-n- or i-propylamino, methylethylamino, methyl-n propylamino, methyl-i propylamino, cyclopropylamino, phenylamino or methyl-phenylamino,
represent phenyl, phenoxy or phenylthio, where each of these radicals may be mono- to trisubstituted by identical or different substituents selected from the group consisting of fluorine, chlorine, bromine, methyl, ethyl, n- or i-propyl, methoxy, ethoxy, n- or i-propoxy, trifluoromethyl and trifluoromethoxy; or represent cyclopropyl, cyclopentyl, cyclohexyl, cyclopropyloxy, cyclopentyloxy, cyclohexyloxy, cyclopropylthio, cyclopentylthio, cyclohexylthio, cyclopropylamino, cyclopentylamino, cyclohexylamino, 1pyrrolidinyl, 1-piperidinyl, and 1-morpholinyl, where each of these radicals may be mono- to trisubstituted by identical or different substituetns selected from the group consisting of fluorine, chlorine, bromine, methyl, ethyl, n- or i-propyl and trifluoromethyl, or
represent pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridyl, pyrimidyl, pyrazinyl or pyridazinyl, where each of these radicals may be mono- or disubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and ethoxyiminoethyl, or represent pyrrolidinyl, piperidinyl, morpholinyl or piperazinyl, each of which is optionally mono- or disubstituted by methyl.
$R^6$ and $R^7$ furthermore together with the phosphorus atom to which they are attached represent in particular a 5- or 6-membered heterocyclyl radical which may contain one or two other identical or different heteroatoms, such as oxygen, sulphur and/or nitrogen, and may be mono- to trisubstituted by identical or different substituents selected from the group consisting of methyl, ethyl, nor i-propyl, methoxy, ethoxy, n- or i-propoxy, chlorine and trifluoromethyl.

The abovementioned general or preferred radical definitions apply both to the end products of the formula (1) and also correspondingly to the starting materials or intermediates required in each case for the preparation.

Preferred compounds according to the invention are also addition products of acids and those fused azole derivatives of the formula (I) in which $R^1$, $R^2$, G and A have the meanings which have been mentioned as being preferred for these radicals.

The acids which can be added preferably include hydrohalic acids, such as, for example, hydrochloric acid and hydrobromic acid, in particular hydrochloric acid, furthermore phosphoric acid, sulphuric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalenedisulphonic acid, saccharine and thiosaccharine.

Compounds according to the invention which are also preferred are addition products of salts of metals of main groups II to IV and subgroups I and II and IV to VIII of the Periodic Table of the Elements and those fused azole derivatives of the formula (I) in which $R^1$, $R^2$, G and A have the meanings which have been mentioned as being preferred for these radicals.

Here, particular preference is given to salts of copper, zinc, manganese, magnesium, tin, iron and nickel. Suitable anions of these salts are those which are derived from acids which lead to physiologically tolerable addition products. Acids of this kind which are particularly preferred in this context are the hydrohalic acids, such as, for example, hydrochloric acid and hydrobromic acid, furthermore phosphoric acid, nitric acid and sulphuric acid.

Examples of substances according to the invention which may be mentioned are the fused azole derivatives listed in Tables 1 to 11 below:

TABLE 1

(I-c)

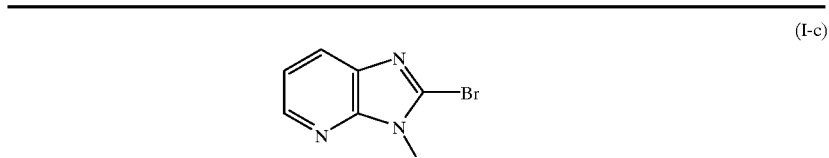

where A represents the following substituents:

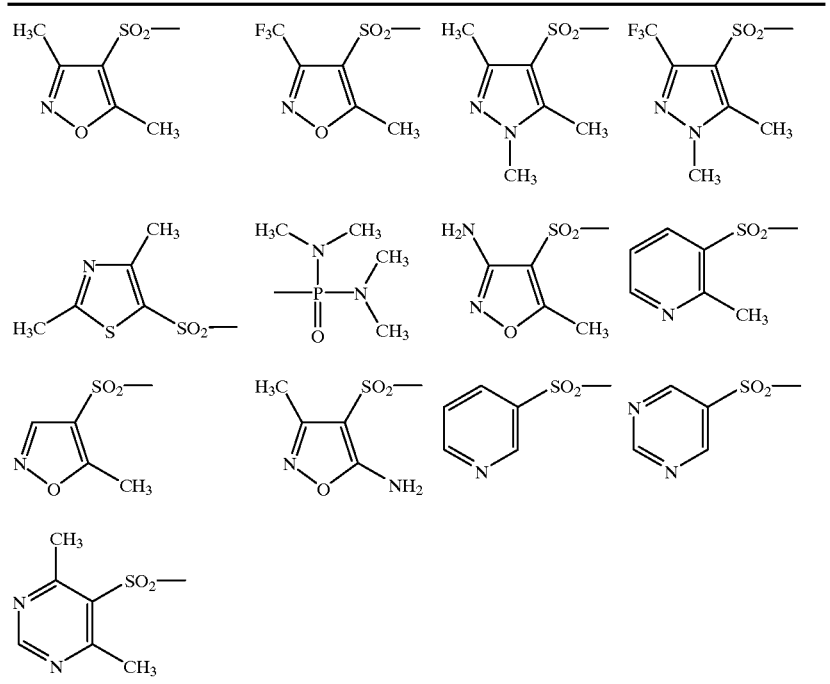

TABLE 2

(I-d)

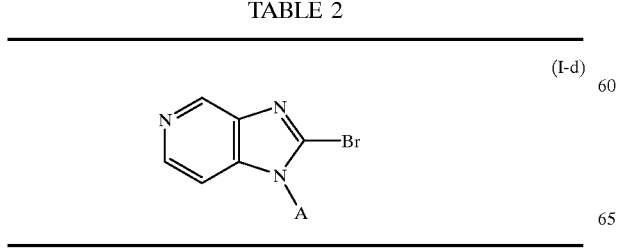

where A represents the substituents mentioned in Table 1.

TABLE 3

(I-e)

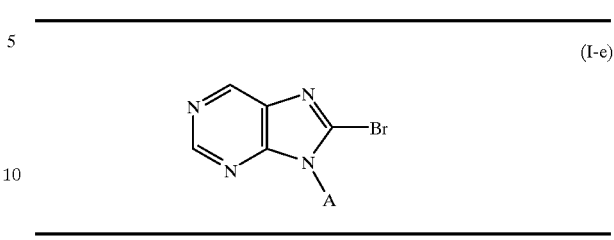

where A represents the substituents mentioned in Table 1.

TABLE 4

(I-f)

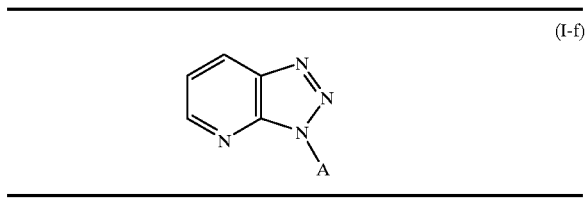

where A represents the substituents mentioned in Table 1.

TABLE 5

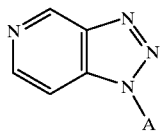
(I-g)

where A represents the substituents mentioned in Table 1.

TABLE 6

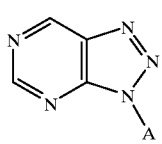
(I-h)

where A represents the substituents mentioned in Table 1.

TABLE 7

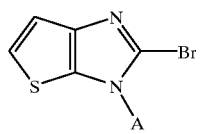
(I-i)

where A represents the substituents mentioned in Table 1.

TABLE 8

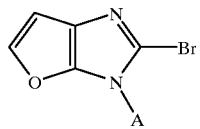
(I-j)

where A represents the substituents mentioned in Table 1.

TABLE 9

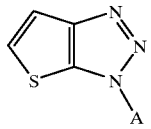
(I-k)

where A represents the substituents mentioned in Table 1.

TABLE 10

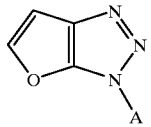
(I-l)

where A represents the substituents mentioned in Table 1

TABLE 11

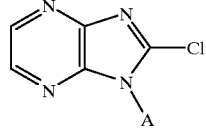
(I-m)

where A represents the substituents mentioned in Table 1.

Using, for example, 2-bromo-1H-imidazo[4,5-b]pyridine and thiophene-2-sulphonyl chloride as starting materials, the course of the process (a) according to the invention can be illustrated by the following equation:

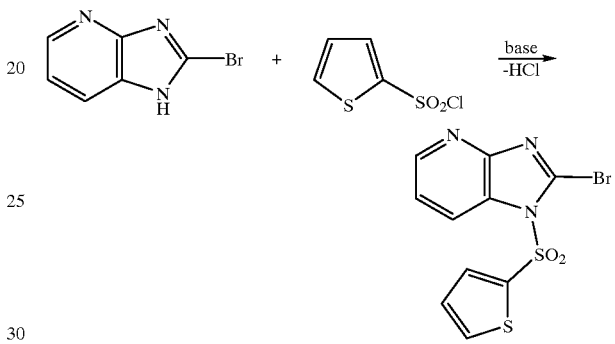

The formula (II) provides a general definition of the azoles required as starting materials for carrying out the process (a) according to the invention. In this formula (II), $R^1$, $R^2$ and G preferably or in particular have those meanings which have already been mentioned in conjunction with the description of the compounds of the formula (I) according to the invention as being preferred or as being particularly preferred for $R^1$, $R^2$ and G.

The azoles of the formula (II) are known (compare, for example, Chem. Ber. 85 (1952) 1012, 1020; Arch. Pharm. 290 (1957) 20, 31; Chem. Ber. 60 (1927), 773; and FR-A 2 542 742).

The formula (III) provides a general definition of the halides furthermore required as starting materials for carrying out the process (a) according to the invention. In this formula (III), A preferably or in particular has those meanings which have already been mentioned in connection with the description of the compounds of the formula (I) according to the invention as being preferred or as being particularly preferred for A. $X^1$ preferably represents chlorine.

The halides of the formula (E) are known or can be prepared by processes known per se (compare, for example, J. Heterocyclic Chem. 1981, 997–1006).

Suitable diluents for carrying out the process (a) according to the invention are all inert organic solvents. Preferably utilizable are aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2- dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate, or ethyl acetate; sulphoxides, such as dimethyl sulphoxide; sulphones, such as sulpholane, or amines, such as pyridine.

Suitable acid binders for carrying out the process (a) according to the invention are all customary inorganic or organic bases. Preferably utilizable are alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (a) according to the invention, the reaction temperatures can be varied within a relatively wide range. In general, the reaction is carried out at temperatures between 0° C. and 150° C., preferably at temperatures between 20° C. and 120° C.

For carrying out the process (a) according to the invention, generally from 1 to 15 mol, preferably from 1 to 2 mol, in particular from 1 to 1.3 mol, of halide of the formula (III) are employed per mole of azole of the formula (II). Work-up is carried out by customary methods.

Using, for example, 1-(thiophene-2-sulphonyl)-1H-imidazo[4,5-b]pyridine-2carbonitrile as starting material and hydrogen sulphide as reaction component, the course of the process (b) according to the invention can be illustrated by the following equation:

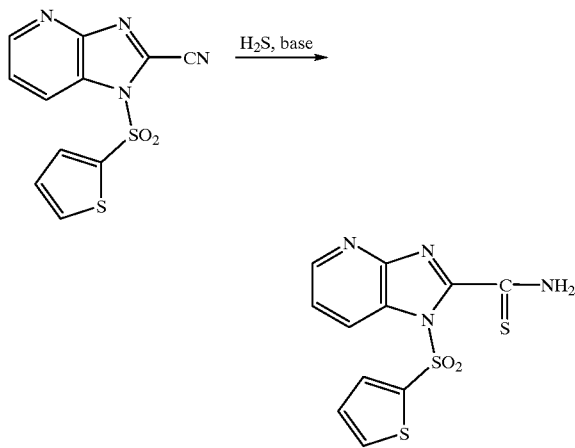

The formula (1-a) provides a general definition of the cyanoimidazoles required as starting materials for carrying out the process (b) according to the invention. In this formula, $R^1$, $R^2$ and A preferably or in particular have those meanings which have already been mentioned in connection with the description of the compounds of the formula (I) according to the invention as being preferred or as being particularly preferred for $R^1$, $R^2$ and A.

The cyanoimidazoles of the formula (I-a) are compounds according to the invention and can be prepared by the process (a) according to the invention.

Suitable diluents for carrying out the process (b) according to the invention are all customary inert organic solvents and also water- Preferably utilizable are aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2- dimethoxyethane, 1,2-diethoxyethane or anisole; amides, such as N,N-dimethylformamide, N,N-dimethylacetamide, N-methyl-formanilide, N-methylpyrrolidone or hexamethylphosphoric triamide; esters such as methyl acetate or ethyl acetate; sulphoxides, such as dimethyl sulphoxide; sulphones, such as sulpholane; amines, such as pyridine; alcohols, such as methanol, ethanol, nor i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

Suitable bases for carrying out the process (b) according to the invention are again all customary inorganic or organic acid binders. Preferably utilizable are alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine triethylamine tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (b) according to the invention, the reaction temperatures can be varied within a relatively wide range. In general, the reaction is carried out at temperatures between 0° C. and 150° C., preferably at temperatures between 20° C. and 120° C.

For carrying out the process (b) according to the invention, generally from 1 to 1000 mol, preferably from 1 to 50 mol, of hydrogen sulphide are employed per mole of cyanoimidazole of the formula (1-a). The practice of the reaction and the work-up are carried out by customary methods.

Using, for example, 1-(thiophene-2-sulphonyl)-1H-imidazo[4,5-b]pyridine-2thiocarboxamide and iodomethane as starting materials, the course of the process (c) according to the invention can be illustrated by the following equation:

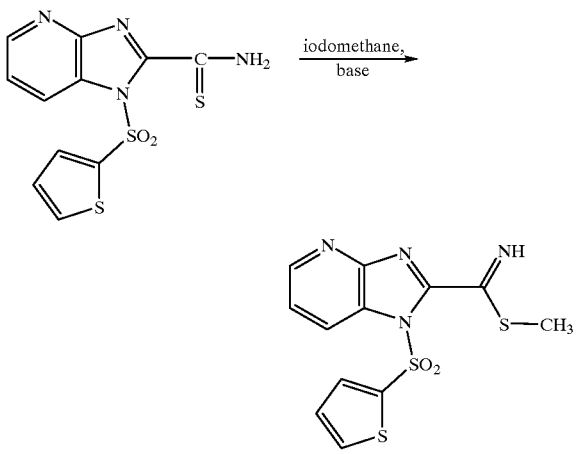

The formula (I-b) provides a general definition of the thiocarbamoyl imidazoles required as starting materials for carrying out the process (c) according to the invention. In this formula, $R^1$, $R^2$ and A preferably or in particular have those meanings which have already been mentioned in connection with the description of the compounds of the formula (1) according to the invention as being preferred or as being particularly preferred for $R^1$, $R^2$ and A.

The thiocarbamoyl imidazoles of the formula (I-b) are compounds according to the invention and can be prepared by the process (b) according to the invention.

The formula (IV) provides a general definition of the alkylating agents furthermore required as starting materials for carrying out the process (c) according to the invention. In this formula, $R^4$ preferably or in particular has those meanings which have already been mentioned in connection with the description of the compounds of the formula (I) according to the invention as being preferred or as being particularly preferred for $R^4$. $X^2$ preferably represents halogen, methanesulphonyloxy, toluenesulphonyloxy, $R^4$—O—$SO_2$—O— or $R^4$—O—CO—O—.

The alkylating agents of the formula (IV) are customary laboratory chemicals.

Suitable diluents for carrying out the process (c) according to the invention are all inert organic solvents. Preferably utilizable are aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; sulphones, such as sulpholane; or amines, such as pyridine.

Suitable acid binders for carrying out the process (c) according to the invention are all customary inorganic or organic bases. Preferably utilizable are alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (c) according to the invention, the reaction temperatures can be varied within a relatively wide range. In general, the reaction is carried out at temperatures between 0° C. and 150° C., preferably at temperatures between 20° C. and 120° C.

For carrying out the process (c) according to the invention, generally from 1 to 10 mol, preferably from 1 to 5 mol, of alkylating agent of the formula (IV) are employed per mole of thiocarbamoyl imidazole of the formula (I-b). Work-up is carried out by customary methods.

The processes (a), (b) and (c) according to the invention are generally carried out under atmospheric pressure. However, it is also possible to operate under elevated or reduced pressure—in general between 0.1 bar and 10 bar.

The fused azole derivatives of the formula (I) can be converted into acid addition salts or metal salt complexes.

For preparing acid addition salts of the compounds of the formula (I), preference is given to using those acids which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off, and, if appropriate, be purified by washing with an inert organic solvent.

For preparing metal salt complexes of the compounds of the formula (I), preference is given to using those salts of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding it to compounds of the formula (I). Metal salt complexes can be isolated in a known manner, for example by filtering off, and they can be purified, if appropriate, by recrystallization.

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimum;*
Phytophthora species, such as, for example, Phytophthora infestans;
Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, Puccinia recondita;
Sclerotinia species, such as, for example, *Sclerotinia sclerotiorum*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in fruit and vegetable growing and viticulture, such as, for example, against Phytophthora species.

The active compounds according to the invention may also be employed to increase the yield of crops. Moreover, they show reduced toxicity and are well tolerated by plants.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components. Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazolecis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5,-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d] pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro [4.5]decane-2-methaneamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophene dicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidine amine,
N-(4-hexylphenyl)-1,4,5,6-tetrahydro-2-pyrimidine amine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methaneimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin,
*bacillus thuringiensis*, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, N-[(6-chloro-3-pyridinyl)-methyl]-N'-cyano-N-methyl-ethaneimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate,
dimethylvinphos, dioxathion, disulphoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulphenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulphotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
varnidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When using the active compounds according to the invention as fungicides, the application rates can be varied within a relatively wide range, depending on the application method. In the treatment of parts of plants, the active compound application rates are, in general, between 0.1 and 10,000 g/ha, preferably between 10 and 1000 g/ha. In the treatment of seed, the active compound application rates are generally between 0.001 and 50 g per kilogram of seed, preferably between 0.01 and 10 g per kilogram of seed. In the treatment of the soil, the active compound application rates are generally between 0.1 and 10,000 g/ha, preferably between 1 and 5000 g/h.

The preparation and the use of the active compounds according to the invention is illustrated by the examples below.

PREPARATION EXAMPLES

Example 1

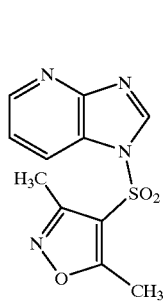

Process (a):

0.3 g (10 mmol) of sodium hydride (80% strength suspension in mineral oil) is added to a solution of 2.5 g (15 mmol) of 1H-imidazo[4,5-b]pyridine in 40 ml of absolute tetrahydrofuran. The mixture is stirred at 20° C. for 10 minutes. 3.0 g (15 mmol) of 3,5-dimethylisoxazole-4-sulphonyl chloride are then added, and the mixture is stirred at 20° C. for another 20 hours. The reaction mixture is poured into 200 ml of water. The resulting mixture is extracted twice with 150 ml of diethyl ether each time. The combined organic phases are dried over sodium sulphate and concentrated under reduced pressure. The residue is chromatographed over silica gel using diethyl ether.

This gives 1.3 g (46% of theory) of 1-(3,5-dimethyl-isoxazole-4-sulphonyl)-1H-imidazo[4,5-b]pyridine as a white solid having a melting range of from 77 to 80° C.

Example 2

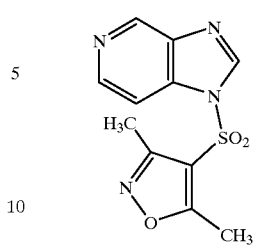

Process (a):

1.4 g (10 mmol) of potassium carbonate are added to a solution of 1.2 g (10 mMol) of 1H-imidazo[4,5-c]pyridine in 30 ml of acetonitrile, and the mixture is stirred at 20° C. for 10 minutes. The mixture is then admixed with 1.9 g (10 mmol) of 3,5dimethylisoxazole-4-sulphonyl chloride and stirred at 20° C. for 20 hours. The reaction mixture is subsequently poured into 150 ml of water. The resulting mixture is extracted twice with 70 ml of ethyl acetate each time. The combined organic phases are dried over sodium sulphate and concentrated under reduced pressure. The residue is stirred with 20 ml of petroleum ether and the resulting solid is filtered off land dried.

This gives 1.6 g (57% of theory) of 1-(3,5-dimethyl-isoxazole-4-sulphonyl)-1H-imidazo[4,5-c]pyridine as a yellow solid of melting point 130–135° C.

The substances listed in Table 12 below are also prepared by the methods given above.

TABLE 12

(I-n)

| Ex. No. | | $R^5$ | Physical constants |
|---|---|---|---|
| 3 | | | m.p.: 190–195° C. |
| 4 | | | $^1$H NMR*: 2.10 |

TABLE 12-continued (I-n)

| Ex. No. | R² | R⁵ | Physical constants |
|---|---|---|---|
| 5 | 3-methyl-imidazo[4,5-b]pyridin-1-yl | 3,4-dimethyl-5-methylisoxazole | ¹H NMR*: 2.43 |
| 6 | 3-methyl-imidazo[4,5-b]pyridin-1-yl | 5-amino-3,4-dimethylisoxazole | ¹H NMR*: 2.21 |
| 7 | 2-bromo-3-methyl-imidazo[4,5-b]pyridin-1-yl | 5-amino-3,4-dimethylisoxazole | ¹H NMR*: 2.19 |
| 8 | 1-methyl-imidazo[4,5-b]pyridin-3-yl | 5-amino-3,4-dimethylisoxazole | ¹H NMR*: 2.30 |
| 9 | 1-methyl-triazolo[4,5-b]pyridin-1-yl | 3,4-dimethyl-5-methylisoxazole | m.p.: 207° C.<br>¹H NMR*: 2.28 |
| 10 | 1-methyl-triazolo[4,5-b]pyridin-1-yl | 5-cyclopropyl-3,4-dimethylisoxazole | ¹H NMR*: 3.01 |
| 11 | 3-methyl-imidazo[4,5-b]pyridin-1-yl | 5-cyclopropyl-3,4-dimethylisoxazole | m.p.: 177° C.<br>¹H NMR: 2.35 |

TABLE 12-continued (I-n)

| Ex. No. | R⁵ | | Physical constants |
|---|---|---|---|
| 12 | [imidazo[4,5-b]pyridine] | [4-methyl-5-cyclopropyl-1H-pyrazole] | ¹H NMR*: 2.56 |
| 13 | [imidazo[4,5-b]pyridine] | [4-methyl-5-cyclopropyl-isoxazole] | m.p.: 106° C.<br>¹H NMR*: 2.48 |
| 14 | [triazolo[4,5-b]pyridine] | [4-methyl-5-cyclopropyl-1H-pyrazole] | ¹H NMR*: 2.89 |

*The ¹H NMR spectra were recorded in deuterochloroform (CDCl₃) or hexadeuterodimethylsulphoxide (DMSO-d₆) using tetramethylsilane (TMS) as internal standard. The chemical shift is given as δ value in ppm.

Use Examples

Example A

Plasmopara Test (grapevine)/protective
Solvent: 47 parts by weight of acetone
Emulsifier: 3 parts by weight of alkyl-aryl polyglycol ether To produce a suitable preparation of the active compound, 1 part by weight of active compound is mixed with the stated amounts of solvent and emulsifier, and the concentrate is diluted with water to the desired concentration.

To test for protective activity, young plants are sprayed with a preparation of active compound at the stated application rate. After the spray coating has dried on, the plants are inoculated with an aqueous spore suspension of Plasmopara viticola and then remain in an incubation cabin at approximately 20° C. and 100% relative atmospheric humidity for 1 day. The plants are then placed in a greenhouse at approximately 21° C. and approximately 90% atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

Active compounds, application rates and test results are shown in the table below.

TABLE A

Plasmopara Test (grapevine)/protective

| Active compound | Application rate of active compound in g/ha | Efficacy in % |
|---|---|---|
| According to the invention: | | |
| (1) [structure] | 100 | 93 |

TABLE A-continued

Plasmopara Test (grapevine)/protective

| Active compound | Application rate of active compound in g/ha | Efficacy in % |
|---|---|---|
| (2) [imidazo-pyridine with SO2-isoxazole, CH3 groups] | 100 | 90 |
| (3) [imidazo-pyrimidine with SO2-isoxazole, CH3 groups] | 100 | 90 |
| (6) [imidazo-pyridine with SO2-isoxazole, CH3, NH2 groups] | 100 | 74 |
| Known from DE-A 195 23 446: [benzotriazole with SO2-isoxazole, CH3] | 100 | 49 |

Example B

Venturia Test (Apple)/protective
Solvent: 47 parts by weight of acetone
Emulsifier: 3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, whereas an efficacy of 100% means that no infection is observed.

Active compounds, application rates and test results are shown in the table below.

TABLE B

Venturia Test (Apple) / protective

| Active compound | Application rate of active compound in g/ha | Efficacy in % |
|---|---|---|
| According to the invention: | | |
| (1) [imidazo-pyridine with SO2-isoxazole, CH3 groups] | 100 | 100 |
| (2) [imidazo-pyridine with SO2-isoxazole, CH3 groups] | 100 | 95 |
| (3) [imidazo-pyrimidine with SO2-isoxazole, CH3 groups] | 100 | 92 |
| [imidazo-pyridine with SO2-isoxazole, CH3, NH2 groups] | 100 | 89 |

TABLE B-continued

Venturia Test (Apple) / protective

| Active compound | Application rate of active compound in g/ha | Efficacy in % |
|---|---|---|
| (6) Known from DE-A 195 23 446: 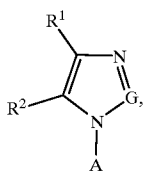 | 100 | 0 |

What is claimed is:

1. A fused azole derivative of the formula

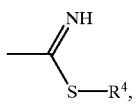

(I)

in which

R$^1$ and R$^2$ together with the carbon atoms to which they are attached represent a [4,5b] pyridine radical, which may be mono- or disubstituted by identical or different substituents selected from the group consisting of fluorine, chlorine, bromine, cyano, nitro, amino, hydroxyl, formyl, carboxyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethoxy, difluoromethylthio, trifluoromethylthio, trifluoromethylsulfinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl, and ethoxyiminoethyl G represents a grouping

R$^3$ represents hydrogen, fluorine, chlorine, bromine, iodine, cyano, nitro, trifluoromethyl, thiocarbamoyl, thiocyanato or the grouping R$^4$ represents methyl or ethyl A represents the grouping —SO$_2$—R$^5$, in which R$^5$ represents isoxazolyl, which may be mono to disubstituted by identical or different substituents selected from the group consisting of fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or 1-propoxy, methyl, ethyl, n- or i-propyl, n-, i-, s- or t-butyl, methoxy, ethoxy, n- or I-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomehtyl, methoxyiminoethyl and ethoxyiminoethyl.

2. A fused azole derivative of the formula

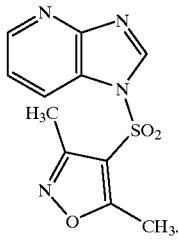

3. A fused azole derivative of the formula

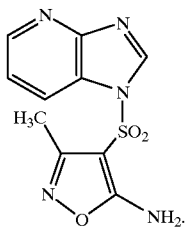

4. A microbicidal composition comprising a microbicidally effective amount of a compound as claimed in claim 1 addition to an extender selected from the group consisting of liquid solvents, liquefied gases under pressure, and solid carriers, and/or a surfactant.

5. A method for controlling undesirable microorganisms in crop protection and In the protection of materials, comprising applying a microbicidally effective amount of a fused azole derivative of the formula (I) according to claim 1 to the microorganisms and/or their habitat.

* * * * *